(12) United States Patent
Li et al.

(10) Patent No.: US 11,839,376 B2
(45) Date of Patent: Dec. 12, 2023

(54) HAND-HELD ELECTROMECHANICAL SURGICAL INSTRUMENTS

(71) Applicant: Covidien LP, Mansfield, MA (US)

(72) Inventors: Shouwei Li, Shanghai (CN); Yezhou Wu, Shanghai (CN); Fen Du, Shanghai (CN); Zhihua Zhang, Shanghai (CN)

(73) Assignee: COVIDIEN LP, Mansfield, MA (US)

( * ) Notice: Subject to any disclaimer, the term of this patent is extended or adjusted under 35 U.S.C. 154(b) by 66 days.

(21) Appl. No.: 17/628,696

(22) PCT Filed: Aug. 30, 2019

(86) PCT No.: PCT/CN2019/103482
§ 371 (c)(1),
(2) Date: Jan. 20, 2022

(87) PCT Pub. No.: WO2021/017079
PCT Pub. Date: Feb. 4, 2021

(65) Prior Publication Data
US 2022/0265272 A1 Aug. 25, 2022

(30) Foreign Application Priority Data

Jul. 31, 2019 (CN) .......................... 201921228479.9

(51) Int. Cl.
*A61B 17/072* (2006.01)
*A61B 17/00* (2006.01)

(52) U.S. Cl.
CPC .................. *A61B 17/07207* (2013.01); *A61B 2017/00398* (2013.01); *A61B 2017/00473* (2013.01); *A61B 2017/07285* (2013.01)

(58) Field of Classification Search
CPC ................ A61B 17/068; A61B 17/072; A61B 2017/2932; A61B 2017/2943
See application file for complete search history.

(56) References Cited

U.S. PATENT DOCUMENTS 5,433,721 A * 7/1995 Hooven ............... A61B 17/068
606/139
5,443,198 A * 8/1995 Viola ................... A61B 17/115
227/19

(Continued)

FOREIGN PATENT DOCUMENTS

CN 102389324 A 3/2012
CN 109561909 A 4/2019

(Continued)

OTHER PUBLICATIONS

International Search Report dated Mar. 17, 2020, issued in corresponding International Appln. No. PCT/ CN2019/103482, 6 pages.

(Continued)

*Primary Examiner* — Gloria R Weeks
(74) *Attorney, Agent, or Firm* — CARTER, DELUCA & FARRELL LLP

(57) ABSTRACT

A handle assembly (12) of a hand-held surgical instrument (10) includes a handle housing (26), a motor (36), and a dual thread lead screw (46) operably coupled to the motor (36) and configured to move proximally and/or distally in response to an actuation of the motor (36). A first thread pitch of the lead screw (46) is suitable for effecting a closing of jaw members (20a, 20b) of an end effector (20), and a second thread pitch of the lead screw (46) is suitable for effecting a stapling function of the end effector (20).

18 Claims, 4 Drawing Sheets

(56) References Cited

U.S. PATENT DOCUMENTS

| | | | |
|---|---|---|---|
| 5,680,981 A | 10/1997 | Mililli et al. | |
| 7,963,433 B2* | 6/2011 | Whitman | A61B 17/072 227/19 |
| 8,616,431 B2* | 12/2013 | Timm | A61B 17/0684 606/167 |
| 8,672,951 B2* | 3/2014 | Smith | A61B 17/115 606/139 |
| 8,752,749 B2* | 6/2014 | Moore | A61B 17/32 227/176.1 |
| 8,967,443 B2* | 3/2015 | McCuen | A61B 34/76 227/175.1 |
| 10,271,841 B2* | 4/2019 | Overmyer | A61B 17/068 |
| 11,045,191 B2* | 6/2021 | Shelton, IV | A61B 17/0686 |
| 11,497,500 B2* | 11/2022 | Xu | A61B 17/07207 |
| 2006/0278680 A1* | 12/2006 | Viola | A61B 17/072 227/176.1 |
| 2007/0260223 A1 | 11/2007 | Scheibe et al. | |
| 2014/0305989 A1* | 10/2014 | Parihar | A61B 17/068 227/176.1 |
| 2017/0135747 A1 | 5/2017 | Broderick et al. | |
| 2018/0116644 A1 | 5/2018 | Householder et al. | |
| 2018/0310983 A1 | 11/2018 | Worrell et al. | |
| 2022/0079586 A1* | 3/2022 | Shelton, IV | A61B 17/32 |

FOREIGN PATENT DOCUMENTS

| | | |
|---|---|---|
| CN | 109620332 A | 4/2019 |
| EP | 3108827 A1 | 12/2016 |
| JP | 2009506799 A | 2/2009 |
| JP | 2009538684 A | 11/2009 |
| JP | 2010540192 A | 12/2010 |
| JP | 2011189136 A | 9/2011 |
| JP | 2018512053 A | 5/2018 |
| JP | 2018519072 A | 7/2018 |

OTHER PUBLICATIONS

Written Opinion of the International Searching Authority dated Mar. 17, 2020, issued in corresponding International Appln. No. PCT/CN2019/103482, 4 pages.

Supplementary Partial European Search Report dated Jul. 13, 2023 for EP Application No. EP19939085 (13 pages).

Office Action dated Jun. 30, 2023 for Japanese Patent Application No. 2022-500884 (11 pages).

* cited by examiner

HAND-HELD ELECTROMECHANICAL SURGICAL INSTRUMENTS

BACKGROUND

1. Technical Field

The disclosure relates to surgical instruments. More specifically, the disclosure relates to hand-held electromechanical surgical instruments that articulate, rotate, and actuate a variety of other functions of surgical attachments, such as, for example, surgical loading units.

2. Background of Related Art

Electromechanical surgical instruments include a reusable handle assembly and disposable loading units and/or single use loading units, such as, for example, surgical end effectors. The end effectors are selectively connected to the handle assembly prior to use and then disconnected from the handle assembly following use in order to be disposed of or in some instances sterilized or reconditioned for re-use. Some handle assemblies may include one or more drive mechanisms for carrying out the operational functions of the end effector.

SUMMARY

In one aspect of the disclosure, a handle assembly of a hand-held surgical instrument is provided and includes a handle housing, a motor disposed within the handle housing, and a lead screw operably coupled to the motor. The lead screw is configured to be translated by the motor to operate a function of an end effector and includes a proximal thread and a distal thread. The proximal thread has a first pitch and the distal thread has a second pitch, different than the first pitch of the proximal thread.

In aspects, the first pitch of the proximal thread may be larger than the second pitch of the distal thread.

In some aspects, the distal thread may correspond with a clamping of an end effector, and the proximal thread may correspond with a stapling function of an end effector.

In another aspect, the handle assembly may further include a gear assembly operably coupling the motor and the lead screw.

In further aspects, the gear assembly may include a first collar disposed about and threadedly coupled to the lead screw, such that a rotation of the first collar translates the lead screw.

In aspects, the first collar may have at least one pin received in the proximal thread or the distal thread of the lead screw.

In some aspects, the gear assembly may include a second collar coupled to the motor. The second collar may have a bevel gear in meshing engagement with a bevel gear of the first collar.

In other aspects, the motor may have a drive shaft extending therefrom. The second collar may be non-rotationally coupled to the drive shaft, such that the second collar rotates with the drive shaft in response to an actuation of the motor.

In further aspects, the bevel gear of the second collar may be angled relative to the bevel gear of the first collar.

In another aspect, the handle housing may include an upper housing portion and a lower housing portion extending downwardly and proximally from the upper housing portion. The upper housing portion may define a longitudinal axis that is parallel with the lead screw.

In aspects, the lower housing portion may define a longitudinal axis disposed at an angle less than 90 degrees relative to the longitudinal axis of the upper housing portion.

In some aspects, the handle assembly may further include an outer tube disposed about the lead screw and pinned to the lead screw. The lead screw may be configured to rotate in response to a manual rotation of the outer tube.

In further aspects, the handle assembly may further include a cap covering a proximal end of the outer tube and detachably coupled to the handle housing. The cap may be configured to resist rotation of the outer tube and, in turn, the lead screw, relative to the handle housing.

In accordance with another aspect of the disclosure, a handle assembly of a hand-held surgical instrument is provided and includes a handle housing, a motor supported by the handle housing, a lead screw operably coupled to the motor, a knob housing coupled to the handle housing, and a shaft portion. The lead screw is configured to move proximally and/or distally in response to an actuation of the motor. The lead screw has a dual thread configured to effect discrete functions of an end effector. The shaft portion has a proximal end portion coupled to the knob housing and a distal end portion configured to be coupled to an end effector.

In aspects, the lead screw may include a proximal end portion having a threaded outer surface, and a distal end portion having a threaded outer surface. The threaded outer surface of the proximal end portion may have a different thread pitch than the threaded outer surface of the distal end portion of the lead screw.

In some aspects, the thread pitch of the threaded outer surface of the proximal end portion of the lead screw may be larger than the thread pitch of the threaded outer surface of the distal end portion of the lead screw.

In further aspects, the thread pitch of the threaded outer surface of the distal end portion of the lead screw may correspond with a clamping of an end effector, and the thread pitch of the threaded outer surface of the proximal end portion of the lead screw may correspond with a stapling function of an end effector.

In other aspects, the handle assembly may further include a gear assembly operably coupling the motor and the lead screw. The gear assembly may further include a first collar and a second collar. The first collar may be disposed about and threadedly coupled to the lead screw, such that a rotation of the first collar translates the lead screw. The second collar may be coupled to the motor and may have a bevel gear in meshing engagement with a bevel gear of the first collar.

In another aspect, the first collar may have at least one pin received in the dual thread of the lead screw.

In aspects, the motor may have a drive shaft extending therefrom. The second collar may be non-rotationally coupled to the drive shaft, such that the second collar rotates with the drive shaft in response to an actuation of the motor.

As used herein, the terms parallel and perpendicular are understood to include relative configurations that are substantially parallel and substantially perpendicular up to about + or −10 degrees from true parallel and true perpendicular.

BRIEF DESCRIPTION OF THE DRAWINGS

Embodiments of the disclosure are described herein with reference to the accompanying drawings, wherein.

DETAILED DESCRIPTION

Figure 1:
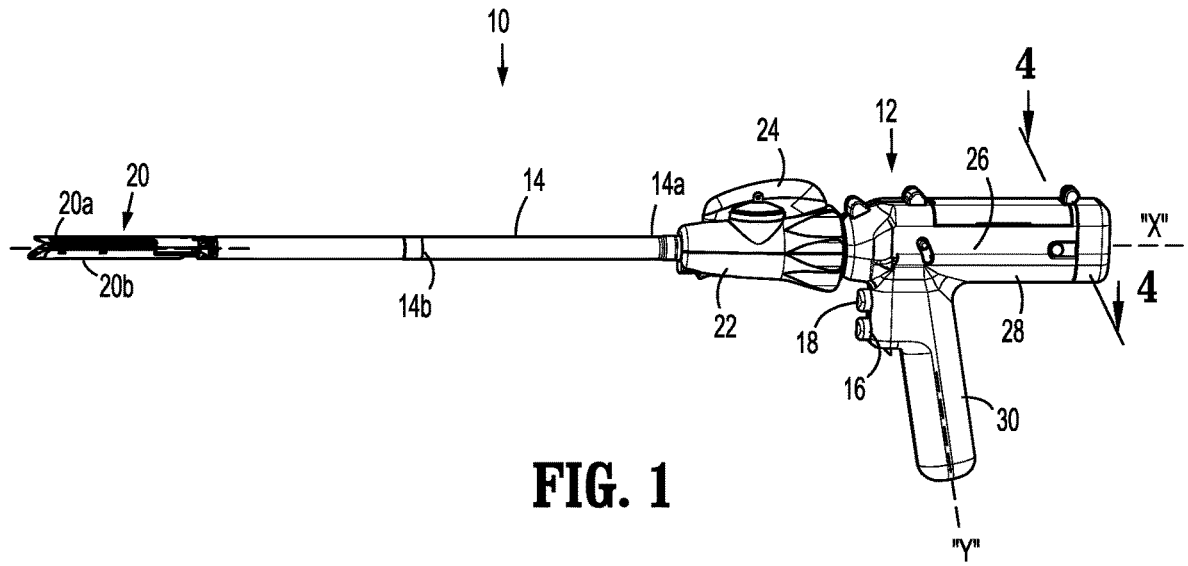
FIG. 1 is a side perspective view of a hand-held electromechanical surgical instrument including a handle assembly, a shaft portion coupled to the handle assembly, and a surgical end effector coupled to the shaft portion, in accordance with an embodiment of the disclosure.

Embodiments of the disclosed surgical instruments are described in detail with reference to the drawings, in which like reference numerals designate identical or corresponding elements in each of the several views. As used herein the term "distal" refers to that portion of the surgical instrument, or component thereof, farther from the user, while the term "proximal" refers to that portion of the surgical instrument, or component thereof, closer to the user.

With reference to FIG. 1, a surgical instrument, in accordance with an embodiment of the disclosure, is generally designated as 10, and is in the form of a powered hand-held electromechanical surgical instrument configured for selective coupling thereto of a plurality of different surgical end effectors, for example, a surgical end effector 20. The end effector 20 is configured for actuation and manipulation by the powered hand-held electromechanical surgical instrument 10.

The hand-held electromechanical surgical instrument 10 includes a handle assembly 12, a knob housing 22 rotationally coupled to the handle assembly 12, and a shaft portion 14 having a proximal end portion 14a coupled to the knob housing 22 and a distal end portion 14b. The knob housing 22 is configured to be manually rotated about a longitudinal axis "X" defined by the shaft portion 14 to rotate the end effector 20 attached to the distal end portion 14b thereof. An articulation lever 24 is rotationally coupled to the knob housing 22 for actuating an articulation of the end effector 20. The handle assembly 12 has a fire switch 16 configured to actuate a stapling and/or cutting function of the end effector 20 and a clamping switch 18 for closing jaw members 20a, 20b of the end effector 20. In aspects, the same switch 16 or 18 may be used to operate the stapling function, the clamping function, and the cutting function of the end effector 20.

Figure 2:
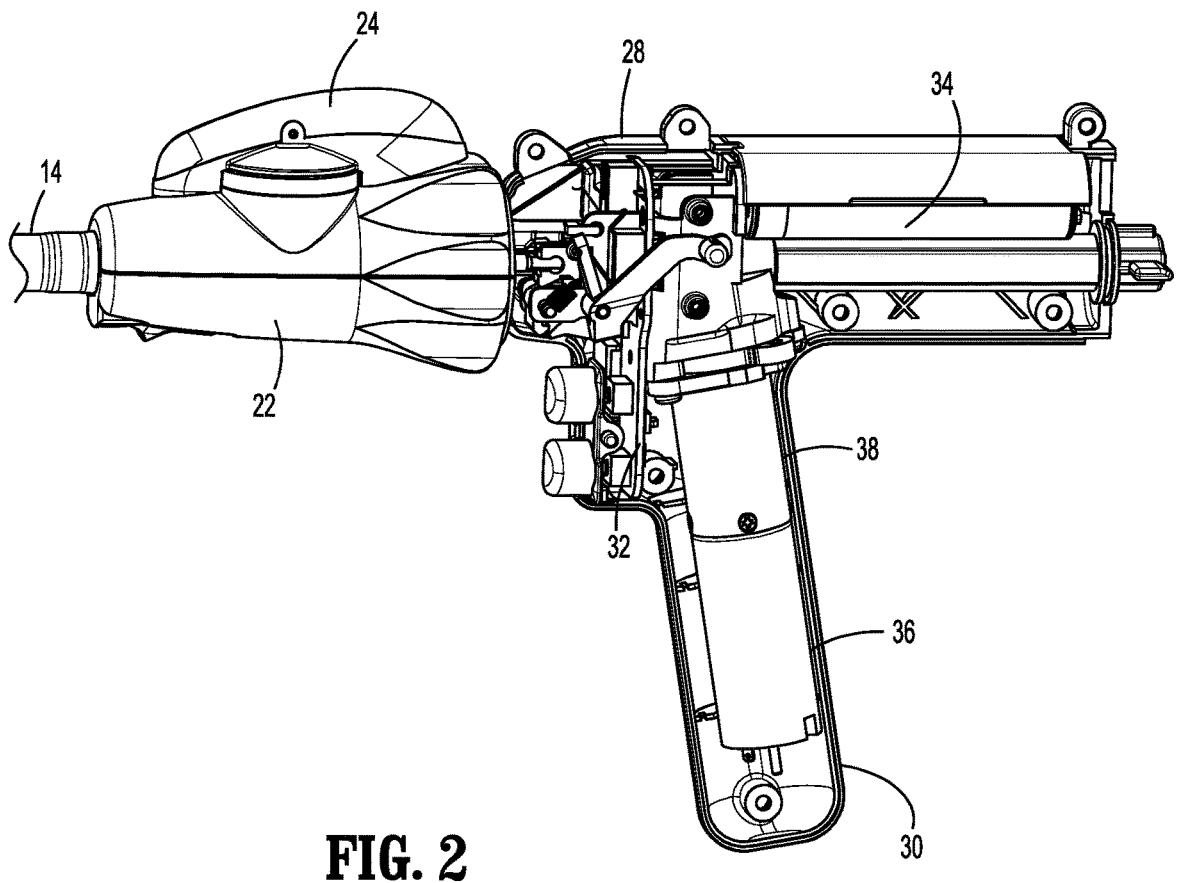
FIG. 2 is an enlarged, side perspective view, with a handle housing half removed, of the surgical instrument of FIG. 1 illustrating internal components of the handle assembly.

With reference to FIGS. 1 and 2, the handle assembly 12 includes a handle housing 26 having an upper housing portion or barrel portion 28 substantially aligned with the longitudinal axis "X," and a lower housing portion or handle portion 30 extending downward and proximally from the upper housing portion 28. The lower housing portion 30 defines a longitudinal axis "Y" disposed at an angle less than 90 degrees (e.g., from about 50 degrees to about 85 degrees) relative to the longitudinal axis "X." The handle assembly 12 includes a printed circuit board 32 extending through both the upper and lower housing portions 28, 30, a battery 34 disposed in the upper housing portion 28, and a motor 36 (e.g., a DC motor) disposed in the lower housing portion 30. The printed circuit board 32 is configured to be in electrical communication (e.g., wirelessly or wired) with the battery 34 and the motor 36. The fire and clamping switches 16, 18 are in communication with the printed circuit board 32 for activating the battery 34 to actuate a clamping function and staple firing and/or cutting function of the end effector 20 and/or the cutting of the tissue.

The motor 36 is drivingly coupled to a gear box 38 that transmits forces generated by the motor 36 into mechanical output. The gear box 38 has a drive shaft 40 coupled to the motor 36 and extending therefrom. The drive shaft 40 is operably coupled to the end effector 20 via a transmission assembly 42, such that rotation of the drive shaft 40 results in a closing of the jaw members 20a, 20b of the end effector 20 and ultimately the firing of staples from the end effector 20.

With reference to FIGS. 3-6, the transmission assembly 42 includes a gear assembly 44 and a lead screw 46. The gear assembly 44 includes a first collar 48 coupled to the lead screw 46 and a second collar 50 coupled to the drive shaft 40 of the gear box 38. The second collar 50 is fixed to the drive shaft 40 and configured to rotate with the drive shaft 40 in response to an actuation of the motor 36. Each of the first and second collars 48, 50 has a respective bevel gear 52, 54 extending radially outward therefrom. The bevel gears 52, 54 of the first and second collars 48, 50 are in meshing engagement with one another, such that a rotation of the second collar 50 results in a rotation of the first collar 48. The bevel gears 52, 54 of the first and second collars 48, 50 are angled relative to one another to allow for the lower housing portion 30 (FIG. 2) of the handle housing 26 to be angled (e.g., from about 50 degrees to about 85 degrees) from the upper housing portion 28, which provides a more ergonomic feel for the clinician.

The first collar 48 is disposed about and threadedly coupled to the lead screw 46, such that a rotation of the first collar 48 translates the lead screw 46. The first collar 48 has at least one pin 56 (FIGS. 5, 7 and 8) received in and extending radially therethrough and which at least one pin 56 is slidably received or disposed in a helical thread of a threaded outer surface of the lead screw 46. In aspects, the first collar 48 may have a threaded inner annular surface threadingly coupled to the threaded outer surface of the lead screw 46.

Figure 3:
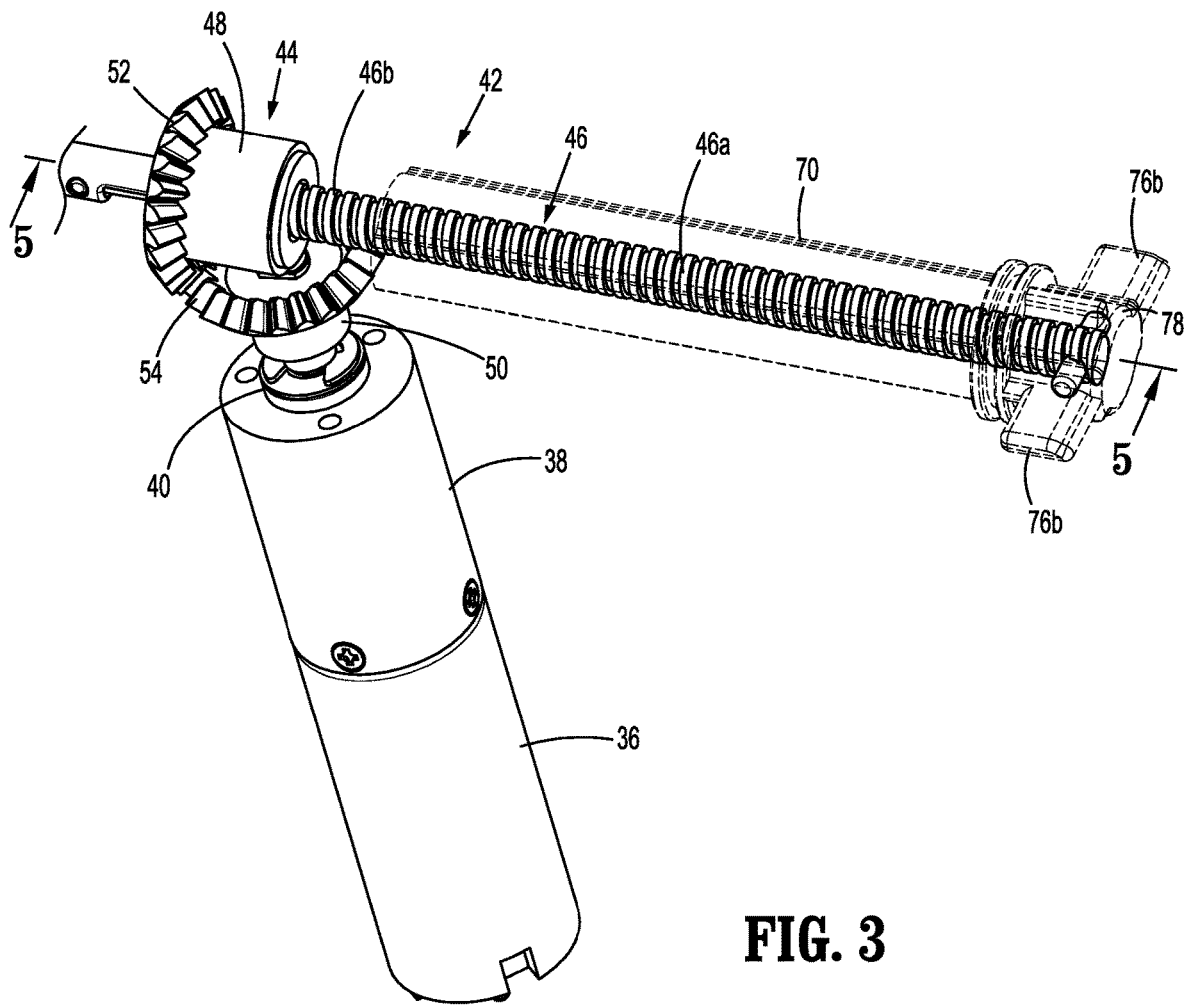
FIG. 3 is a top perspective view illustrating a transmission assembly of the handle assembly of FIG. 2 including a motor, a lead screw, and a gear assembly.
Figure 4:
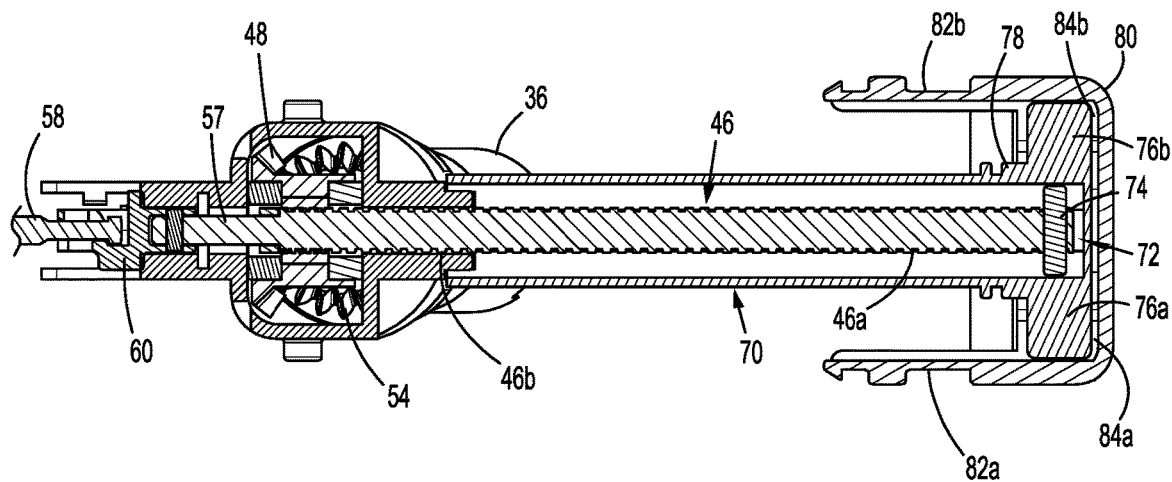
FIG. 4 is a cross-section, taken along lines 4-4 of FIG. 2, with parts removed, illustrating various components of the transmission mechanism.

With reference to FIGS. 3 and 4, the handle assembly 12 includes a screw guide, such as, for example, an outer tube 70, disposed about the lead screw 46. The outer tube 70 defines a longitudinally-extending channel 72 having the lead screw 46 slidably disposed therein. The lead screw 46 may be attached to the outer tube 70 via a pin 74 that allows the lead screw 46 to slide within the outer tube 70 while inhibiting rotation of the lead screw 46 within the outer tube 70. The outer tube 70 has a pair of arms 76a, 76b extending radially outward from a proximal end 78 thereof. The arms 76a, 76b are configured to be grasped by a hand of a clinician for manual rotation of the outer tube 70, and thus the lead screw 46.

The handle assembly 12 may further include a cap 80 for covering and supporting the proximal end 78 of the outer tube 70 therein. The cap 80 may define grooves 84a, 84b therein for receiving the arms 76a, 76b of the outer tube 70 and for inhibiting rotation of the outer tube 70 relative to the cap 80. The cap 80 has a pair of flexible latch arms 82a, 82b extending distally therefrom configured for detachable, snap-fit connection with the upper housing portion 28 (FIG. 2) of the handle housing 26.

The lead screw 46 is coaxial with the longitudinal axis "X" of the upper housing portion 28 and has a proximal end portion 46a and a distal end portion 46b. The distal end portion 46b of the lead screw 46 has a rod 57 extending distally therefrom. The rod 57 is coupled to a fire shaft 58 via a universal coupler 60. The fire shaft 58 is configured to be coupled to a driven shaft (not shown) of the end effector 20 for carrying out the clamping and stapling functions of the end effector 20.

Figure 5:
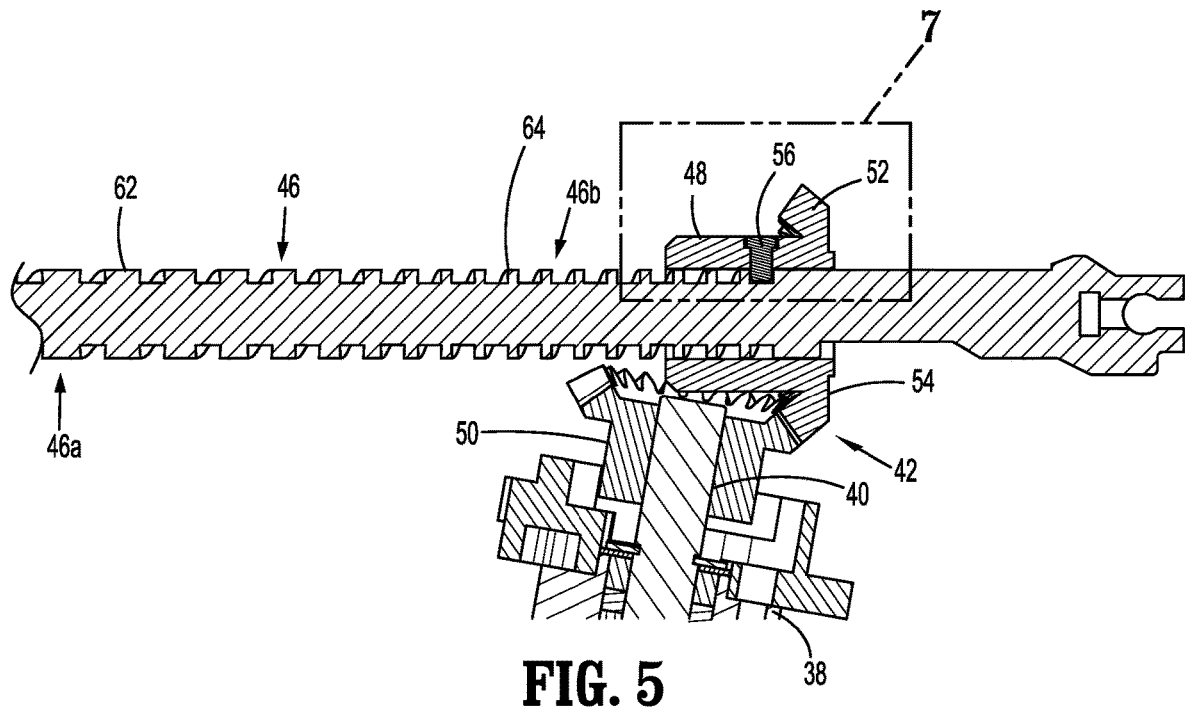
FIG. 5 is a cross-section, taken along lines 5-5 in FIG. 3, with parts removed, illustrating the lead screw and the gear assembly of the transmission mechanism.
Figure 6:
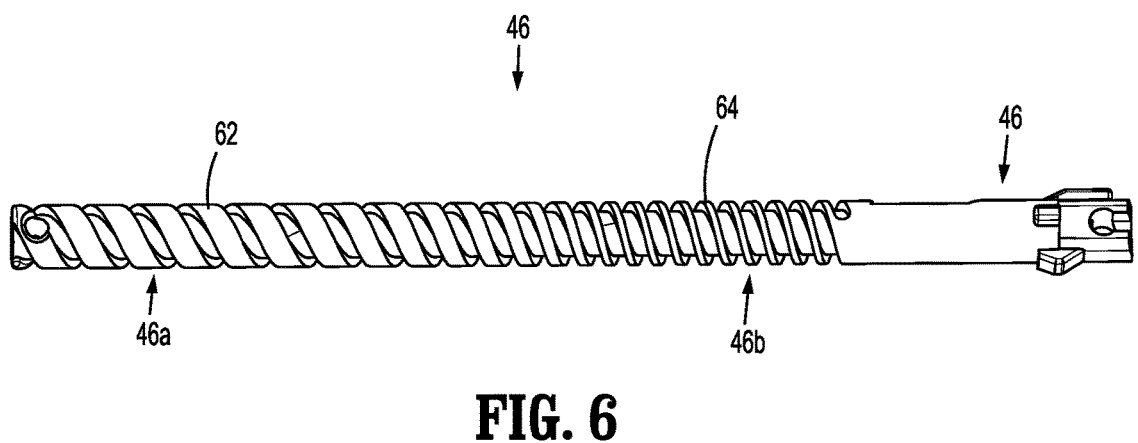
FIG. 6 is a side view illustrating the lead screw of the transmission mechanism of FIG. 3.

As best shown in FIGS. 5 and 6, the lead screw 46 has a dual thread 62, 64, with each being configured to effect the respective functions of the end effector 20, such as, for example, the stapling function and the clamping function. In particular, the proximal end portion 46a of the lead screw 46 has a threaded outer surface 62 having a first thread pitch, and the distal end portion 46b of the lead screw 46 has a threaded outer surface 64 having a second thread pitch, different from the first thread pitch. The thread pitch of the threaded outer surface 62 of the proximal end portion 46a of the lead screw 46 is larger than the thread pitch of the threaded outer surface 64 of the distal end portion 46b of the lead screw 46. In aspects, the lead screw 46 may have a transitional thread between the proximal and distal end portions 46a, 46b. In other aspects, the change in thread pitch between the proximal and distal end portions 46a, 46b may be abrupt.

Due to the thread pitch of the threaded outer surface 62 of the proximal end portion 46a of the lead screw 46 being relatively larger (e.g., about double), the proximal end portion 46a of the lead screw 46 is more suitable for carrying out the stapling function of the end effector 20. For example, the larger thread pitch allows for a greater axial translation of the lead screw 46 per rotation thereof, thereby producing a more rapid actuation of the stapling function of the end effector 20. Due to the thread pitch of the threaded outer surface 64 of the distal end portion 46b of the lead screw 46 being smaller, the distal end portion 46b of the lead screw 46 is more suitable for carrying out the clamping function of the end effector 20. For example, the smaller thread pitch allows for a more finely controlled opening and closing of the jaw members 20a, 20b of the end effector 20 as a result of the lead screw 46 translating a lesser distance per rotation thereof, and for a more controlled rate of compression of tissue disposed between the jaw members 20a, 20b.

In operation, with tissue received between the jaw members 20a, 20b of the end effector 20, the fire switch 16 may be actuated to transfer power from the battery 34 to the motor 36. The motor 36 rotates the drive shaft 40 of the gear box 38, which drives a concomitant rotation of the second collar 50 and the first collar 48. Due to the pin 56 of the first collar 48 being received in the threaded outer surface 64 of the distal end portion 46b of the lead screw 46, rotation of the first collar 48 drives a distal movement of the lead screw 46 to ultimately close the jaw members 20a, 20b of the end effector 20 about the tissue. A continued actuation of the motor 36 eventually advances the distal end portion 46b of the lead screw 46 out of engagement with the first collar 48 and advances the proximal end portion 46a of the lead screw 46 into the first collar 48.

Figure 7:
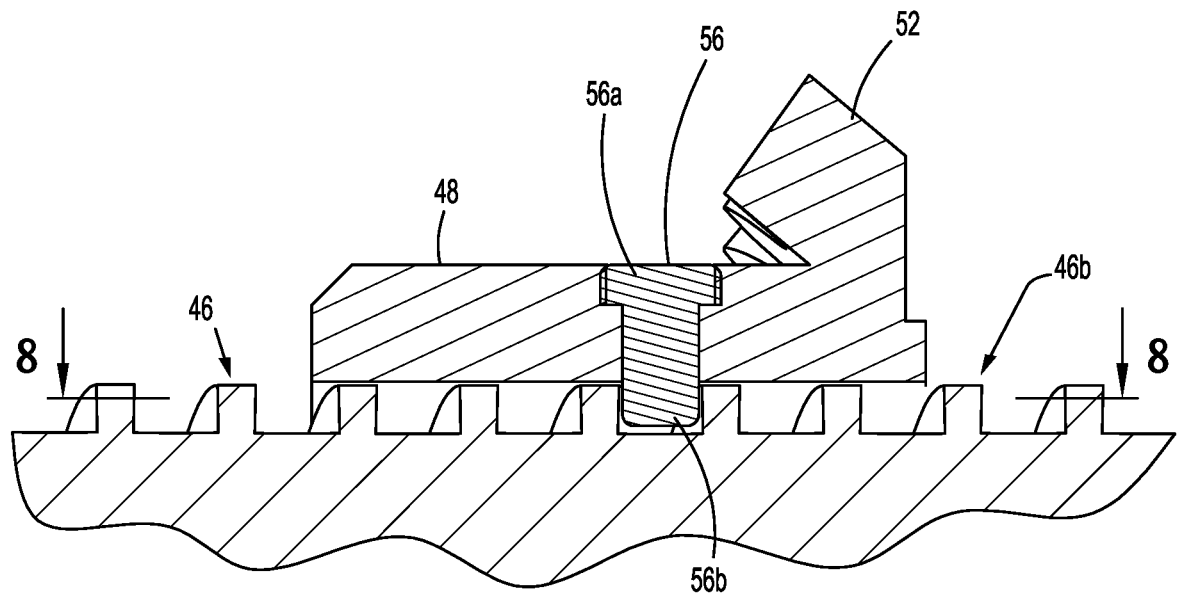
FIG. 7 is an enlarged view of the indicated area of FIG. 5, illustrating the lead screw advanced relative to the gear assembly of the transmission mechanism.
Figure 8:
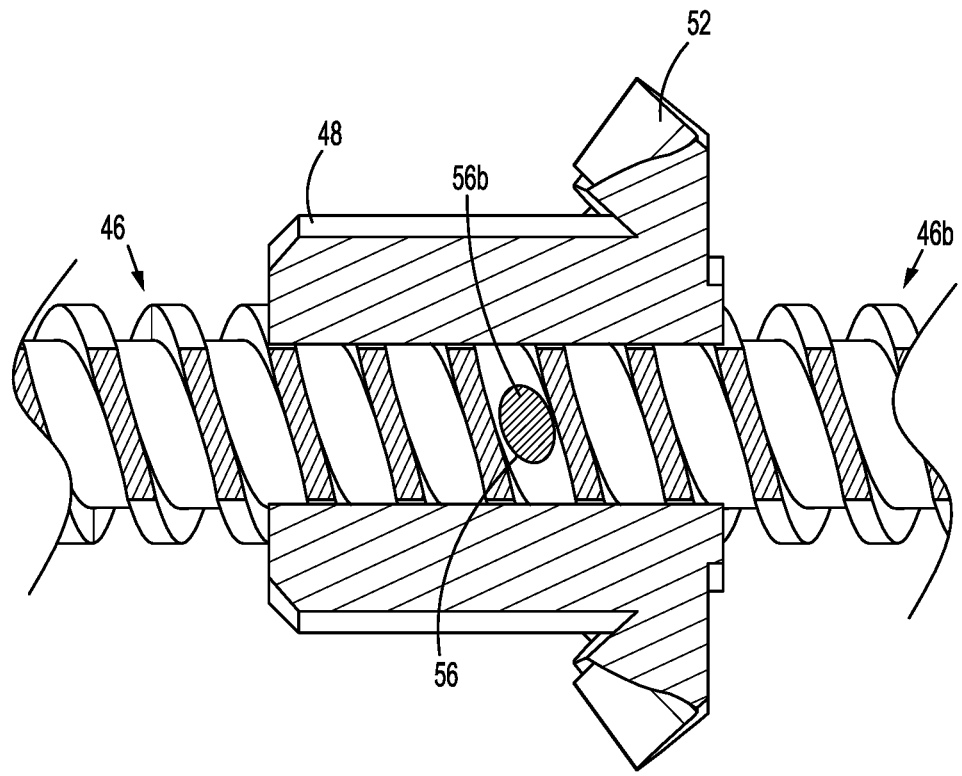
FIG. 8 is a cross-sectional view, as taken through 8-8 of FIG. 7.

With reference to FIGS. 7 and 8, in an embodiment, it is contemplated that pin 56 includes a head portion 56a supported in the first collar 48, and a stem or body portion 56b extending into the helical groove of the lead screw 46. Body portion 56b of pin 56 may have an elliptical, transverse, cross-sectional profile to contacting and sliding along the thread of the lead screw 46. While body portion 56b of a pin 56 having an elliptical, transverse, cross-sectional profile is shown and described, it is contemplated that the body portion 56b may have any shaped transverse cross-sectional profile which is capable of sliding along the thread of the lead screw 46, such as, for example, circular, ovoidal, triangular, crescent, etc. The elliptical, transverse, cross-sectional profile of the body portion 56b of a pin 56 facilitates a transition of pin 56 between the different pitches of the proximal end portion 46a and the distal end portion 46b of the lead screw 46. Additionally, the elliptical, transverse, cross-sectional profile of the body portion 56b of a pin 56 increases the surface area that is in contact between the pin 56 and the thread of the lead screw 46.

With the proximal end portion 46a of the lead screw 46 engaged with the first collar 48, a rotation of the first collar 48 drives a relatively faster distal movement of the lead screw 46 due to the larger thread pitch of the proximal end portion 46a of the lead screw 46, as described above. The relatively fast distal movement of the lead screw 46 rapidly drives staples from the end effector 20 into the tissue clamped between the jaw members 20a, 20b. Additionally, for end effectors 20 including a translatable knife, it is contemplated that distal movement of the lead screw 46 may also result in the distal translation of the knife (not shown) through the tissue to thereby cut the tissue.

In a scenario where the battery 34 is low or dead, or an actuation of the fire switch 16 otherwise fails to result in a desired output, the transmission mechanism 42 may be manually operated. In particular, the cap 80 may be removed from the housing portion 26 to reveal the outer tube 70 of the handle assembly 12. A clinician may grasp the arms 76a, 76b of the outer tube 70 and rotate the outer tube 70 about the longitudinal axis "X." Since the lead screw 46 is pinned to the outer tube 70, the rotation of the outer tube 70 results in a rotation of the lead screw 46 to manually open the end effector 20, close the end effector 20, fire staples from the end effector 20, or cut tissue.

Any of the components described herein may be fabricated from either metals, plastics, resins, composites or the like taking into consideration strength, durability, wearability, weight, resistance to corrosion, ease of manufacturing, cost of manufacturing, and the like.

It will be understood that various modifications may be made to the embodiments of the presently disclosed surgical instruments. Therefore, the above description should not be construed as limiting, but merely as exemplifications of embodiments. Those skilled in the art will envision other modifications within the scope and spirit of the disclosure. For example, any and all features of one described embodiment may be suitably incorporated into another embodiment.

What is claimed is:

1. A handle assembly of a hand-held surgical instrument, comprising:
   a handle housing;
   a motor disposed within the handle housing; and
   a lead screw operably coupled to the motor and configured to be translated by the motor to operate a function of an end effector, wherein the lead screw includes:
   a proximal thread having a first pitch; and
   a distal thread having a second pitch, different than the first pitch of the proximal thread;

and a gear assembly operably coupled to the motor and the lead screw, the gear assembly including a bevel gear on a first collar disposed about and threadedly coupled to the lead screw, such that rotation of the first collar and the bevel gear translates the lead screw.

2. The handle assembly according to claim 1, wherein the first collar has at least one pin received in the proximal thread or the distal thread of the lead screw.

3. The handle assembly according to claim 1, wherein the gear assembly includes a second collar coupled to the motor and having a bevel gear in meshing engagement with a bevel gear of the first collar.

4. The handle assembly according to claim 3, wherein the motor has a drive shaft extending therefrom, the second collar non-rotationally coupled to the drive shaft, such that the second collar rotates with the drive shaft in response to an actuation of the motor.

5. The handle assembly according to claim 3, wherein the bevel gear of the second collar is angled relative to the bevel gear of the first collar.

6. The handle assembly according to claim 5, wherein the handle housing includes:
an upper housing portion defining a longitudinal axis that is parallel with the lead screw; and
a lower housing portion extending downwardly and proximally from the upper housing portion.

7. The handle assembly according to claim 6, wherein the lower housing portion defines a longitudinal axis, the longitudinal axis of the lower housing portion disposed at an angle less than 90 degrees relative to the longitudinal axis of the upper housing portion.

8. The handle assembly according to claim 1, further comprising an outer tube disposed about the lead screw and pinned to the lead screw, wherein the lead screw is configured to rotate in response to a manual rotation of the outer tube.

9. The handle assembly according to claim 8, further comprising a cap covering a proximal end of the outer tube and detachably coupled to the handle housing, wherein the cap is configured to resist rotation of the outer tube and, in turn, the lead screw, relative to the handle housing.

10. The handle assembly according to claim 1, wherein the first pitch of the proximal thread is larger than the second pitch of the distal thread.

11. The handle assembly according to claim 10, wherein the distal thread corresponds with a clamping of an end effector, and the proximal thread corresponds with a stapling function of an end effector.

12. A handle assembly of a hand-held surgical instrument comprising:
a handle housing;
a motor supported by the handle housing;
a lead screw operably coupled to the motor and configured to move at least one of proximally or distally in response to an actuation of the motor, the lead screw having a dual thread configured to effect discrete functions of an end effector;
a knob housing coupled to the handle housing; and
a shaft portion having a proximal end portion coupled to the knob housing and a distal end portion configured to be coupled to an end effector.

13. The handle assembly according to claim 12, wherein the lead screw includes:
a proximal end portion having a threaded outer surface; and
a distal end portion having a threaded outer surface, the threaded outer surface of the proximal end portion having a different thread pitch than the threaded outer surface of the distal end portion of the lead screw.

14. The handle assembly according to claim 13, wherein the thread pitch of the threaded outer surface of the proximal end portion of the lead screw is larger than the thread pitch of the threaded outer surface of the distal end portion of the lead screw.

15. The handle assembly according to claim 14, wherein the thread pitch of the threaded outer surface of the distal end portion of the lead screw corresponds with a clamping of an end effector, and the thread pitch of the threaded outer surface of the proximal end portion of the lead screw corresponds with a stapling function of an end effector.

16. The handle assembly according to claim 12, further comprising a gear assembly operably coupling the motor and the lead screw, the gear assembly including:
a first collar disposed about and threadedly coupled to the lead screw, such that a rotation of the first collar translates the lead screw; and
a second collar coupled to the motor and having a bevel gear in meshing engagement with a bevel gear of the first collar.

17. The handle assembly according to claim 16, wherein the first collar has at least one pin received in the dual thread of the lead screw.

18. The handle assembly according to claim 16, wherein the motor has a drive shaft extending therefrom, the second collar non-rotationally coupled to the drive shaft, such that the second collar rotates with the drive shaft in response to an actuation of the motor.

* * * * *